(12) United States Patent
Nishimi et al.

(10) Patent No.: US 8,367,213 B2
(45) Date of Patent: Feb. 5, 2013

(54) BIOCHEMICAL INSTRUMENT HAVING SURFACE THAT INHIBITS NONSPECIFIC ADSORPTION

(75) Inventors: Taisei Nishimi, Kanagawa (JP); Satoshi Hoshi, Kanagawa (JP); Morihito Ikeda, Kanagawa (JP); Takashi Kubo, Kanagawa (JP); Satoshi Tanaka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 680 days.

(21) Appl. No.: 12/442,978

(22) PCT Filed: Sep. 28, 2007

(86) PCT No.: PCT/JP2007/068992
§ 371 (c)(1),
(2), (4) Date: Mar. 26, 2009

(87) PCT Pub. No.: WO2008/038774
PCT Pub. Date: Apr. 3, 2008

(65) Prior Publication Data
US 2010/0035071 A1  Feb. 11, 2010

(30) Foreign Application Priority Data

Sep. 28, 2006 (JP) ................................. 2006-263906
Jan. 19, 2007 (JP) ................................. 2007-009934

(51) Int. Cl.
*B32B 9/04* (2006.01)
(52) U.S. Cl. .......................... 428/447; 428/446; 428/451
(58) Field of Classification Search .................. 428/447, 428/446, 451
See application file for complete search history.

(56) References Cited

U.S. PATENT DOCUMENTS

2002/0103352 A1   8/2002   Sudor

FOREIGN PATENT DOCUMENTS

| | | |
|---|---|---|
| DE | 10002895 A1 | 7/2001 |
| EP | 1750127 A1 | 7/2007 |
| JP | 02-274260 A | 11/1990 |
| JP | 05-193056 A | 8/1993 |
| JP | 09-176321 A | 7/1997 |
| JP | 09-176322 A | 7/1997 |
| JP | 2000-350770 A | 12/2000 |
| JP | 2004-286538 A | 10/2004 |
| JP | 2005/074139 * | 3/2005 |
| JP | 2005-074139 A | 3/2005 |
| JP | 2005-264135 A | 9/2005 |
| JP | 2005-272506 A | 10/2005 |
| JP | 2006-003163 A | 1/2006 |
| JP | 2006-096806 A | 4/2006 |
| JP | 2006-131823 A | 5/2006 |
| JP | 2006-158961 A | 6/2006 |
| JP | 2006-234758 A | 9/2006 |
| WO | 0065352 A1 | 11/2000 |
| WO | 2004044585 A1 | 5/2004 |
| WO | 2004048603 A3 | 6/2004 |
| WO | 2004048603 A2 | 10/2004 |

OTHER PUBLICATIONS

Extended European Search Report for Application No. 07828733.1 dated Mar. 30, 2010.
H. G. Choi et al., Poly(ethylene glycol) (PEG)-modified poly(dimethylsiloxane) (PDMS) for protein- and cell-resistant surfaces in microbioreactor, Proceedings of microTAS 2003 Seventh International Conference on Micro Total Analysis Systems vol. 2, pp. 1105-1108 (Oct. 5, 2003).
Japanese Office Action dated Jan. 24, 2012 corresponding to JP Application No. 2007-009934.
Official Action dated Aug. 27, 2012 in European Patent Application No. 07828733.1.

* cited by examiner

*Primary Examiner* — Edward Cain
(74) *Attorney, Agent, or Firm* — Sughrue Mion, PLLC

(57) ABSTRACT

An object of the present invention is to provide a biochemical instrument having a surface that can simultaneously inhibit adsorption of a biopolymer and that of a hydrophobic low-molecular-weight compound. The present invention provides a biochemical instrument comprising a region that inhibits adsorption of a hydrophobic low-molecular-weight compound and a region that inhibits adsorption of a biopolymer on the surface of a water-insoluble material.

13 Claims, 1 Drawing Sheet

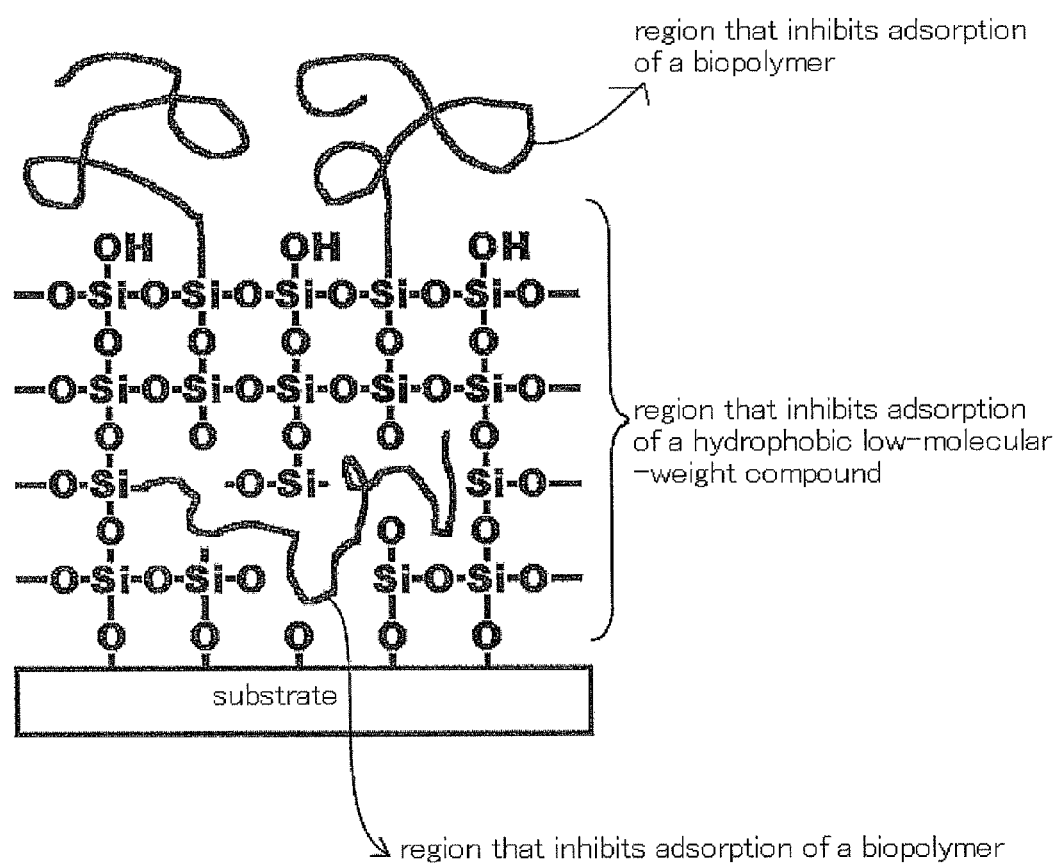

BIOCHEMICAL INSTRUMENT HAVING SURFACE THAT INHIBITS NONSPECIFIC ADSORPTION

TECHNICAL FIELD

The present invention relates to a biochemical instrument having a surface that inhibits nonspecific adsorption. More particularly, the present invention relates to a biochemical instrument having a surface that inhibits nonspecific adsorption of both a hydrophobic low-molecular-weight compound and a biopolymer.

BACKGROUND ART

Surfaces of various types of biochemical instruments, such as containers, flow channels, pipettes, or syringes, are often brought into contact with solutions containing biologically-relevant substances, such as blood, cells, or proteins, or hydrophobic low-molecular-weight compounds, such as pharmaceutical compounds or surfactants. On such surfaces, however, it is preferable that nonspecific adsorption of biologically-relevant substances or hydrophobic low-molecular-weight compounds do not occur. At present, a property such that nonspecific adsorption of biologically-relevant substances or hydrophobic low-molecular-weight compounds would not occur is not imparted to a material that is currently used.

In the case of plastic materials, such as polystyrene or polypropylene, for example, adsorption of a biopolymer (e.g., a protein) or hydrophobic low-molecular-weight compound is not sufficiently inhibited. In the case of polyethylene glycol or an MPC polymer which is a methacrylate copolymer having a phospholipid-like structure, adsorption of a biopolymer is inhibited to some extent, but adsorption of a hydrophobic low-molecular-weight compound is not inhibited. In the case of poly(2-methoxyethyl acrylate) (PMEA) or poly(hydroxyethyl methacrylate) (PHEMA), also, adsorption of a biopolymer is inhibited to some extent, but adsorption of a hydrophobic low-molecular-weight compound is not inhibited. In the case of glass, adsorption of a hydrophobic low-molecular-weight compound is inhibited, but adsorption of a biopolymer is not inhibited.

As described above, a surface that inhibits adsorption of a biopolymer and a surface that inhibits adsorption of a hydrophobic low-molecular-weight compound have been heretofore known; however, it was impossible to simultaneously inhibit adsorption of a biopolymer and that of a hydrophobic low-molecular-weight compound.

[Non-patent document 1] Ishihara, *J. Biomed Mater. Res.* 39, 323-330 (1998)

[Patent document 1] JP Patent Publication (kokai) No. H-11-174057 (A) (1999)

[Patent document 2] JP Patent Publication (kokai) No. 2000-304749 (A)

[Patent document 3] JP Patent Publication (kokai) No. 2001-272406 (A)

[Patent document 4] JP Patent Publication (kokai) No. 2004-290111 (A)

DISCLOSURE OF THE INVENTION

Object to be Solved by the Invention

The present invention is intended to resolve the problems of conventional techniques described above. More specifically, the present invention is intended to provide a biochemical instrument having a surface that can simultaneously inhibit adsorption of a biopolymer and that of a hydrophobic low-molecular-weight compound.

Means for Solving the Object

The present inventors have conducted concentrated studies in order to attain the above objects. As a result, they discovered that a surface that can simultaneously inhibit adsorption of a biopolymer and that of a hydrophobic low-molecular-weight compound can be prepared by providing a region that inhibits adsorption of a hydrophobic low-molecular-weight compound and a region that inhibits adsorption of a biopolymer on the surface of a water-insoluble material. This has led to the completion of the present invention.

The present invention provides a biochemical instrument comprising a region that inhibits adsorption of a hydrophobic low-molecular-weight compound and a region that inhibits adsorption of a biopolymer on the surface of a water-insoluble material.

Preferably, the coverage of the surface of a water-insoluble material with the region that inhibits adsorption of a hydrophobic low-molecular-weight compound and the region that inhibits adsorption of a biopolymer is 90% or more.

Preferably, the region that inhibits adsorption of a hydrophobic low-molecular-weight compound is an inorganic crosslinked polymer or an organic crosslinked polymer.

Preferably, the region that inhibits adsorption of a hydrophobic low-molecular-weight compound comprises a hydrolyzed condensate of a metal alkoxide.

Preferably, the region that inhibits adsorption of a biopolymer is a hydrophilic polymer.

Preferably, the hydrophilic polymer is a non-charged hydrophilic polymer.

Preferably, the non-charged hydrophilic polymer is any of polyethylene glycol, polyvinyl pyrrolidone, polyvinyl alcohol, poly(hydroxyalkyl)methacrylate, polyacrylamide, a polymer having a phosphorylcholine group in a side chain, polysaccharide, or polypeptide.

Preferably, the region that inhibits adsorption of a hydrophobic low-molecular-weight compound and the region that inhibits adsorption of a biopolymer comprise the structure represented by the formula below:

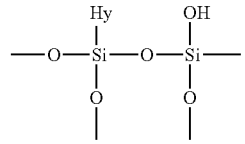

wherein Hy represents a hydrophilic polymer.

Preferably, Hy is any of polyethylene glycol, polyvinyl pyrrolidone, polyvinyl alcohol, poly(hydroxyalkyl)methacrylate, polyacrylamide, a polymer having a phosphorylcholine group in a side chain, polysaccharide, or polypeptide.

Preferably, the water-insoluble material is plastic.

Preferably, the water-insoluble material is any of polystyrene, polypropylene, acrylic polymer, cycloolefin polymer, polyethylene terephthalate(PET), triacetyl cellulose(TAC), polydimethylsiloxane (PDMS), or fluorine resin.

Preferably, an adhesion layer is provided between the water-insoluble material, and the region that inhibits adsorption of a hydrophobic low-molecular-weight compound and the region that inhibits adsorption of a biopolymer.

Preferably, the biochemical instrument according to the present invention is obtained by coating the surface of a water-insoluble material with the solution containing a polymer represented by formula (I) or (II) and crosslinking the polymer:

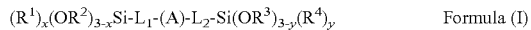   Formula (I)

   Formula (II)

wherein $R^1$ to $R^6$ each independently represent a hydrogen atom or a hydrocarbon group having 8 or fewer carbon atoms; $R^7$ represents a hydrogen atom or a monovalent nonmetal atomic group; x, y, and z each independently represent an integer from 0 to 2; $L^1$ to $L^3$ each independently represent a divalent linking group having 3 or more types of atoms selected from the group consisting of a carbon atom, a hydrogen atom, an oxygen atom, a nitrogen atom, and a sulfur atom; and A and B each independently represent a polymer and an oligomer having structural unit repeats.

Preferably, the biochemical instrument according to the present invention is obtained by coating the surface of a water-insoluble material with the solution containing a polymer represented by formula (III) or (V) and crosslinking the polymer:

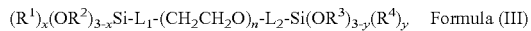   Formula (III)

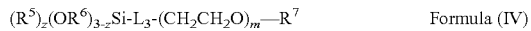   Formula (IV)

N=3 to 25,000; m=3 to 25,000
wherein $R^1$ to $R^6$ each independently represent a hydrogen atom or a hydrocarbon group having 8 or fewer carbon atoms; $R^7$ represents a hydrogen atom or a monovalent nonmetal atomic group; x, y, and z each independently represent an integer from 0 to 2; and $L^1$ to $L^3$ each independently represent a divalent linking group having 3 or more types of atoms selected from a carbon atom, a hydrogen atom, an oxygen atom, a nitrogen atom, and a sulfur atom.

Preferably, crosslinking is carried out by the sol-gel method.

Another aspect of the present invention provides a biosensor comprising the biochemical instrument mentioned above.

Further another aspect of the present invention provides a method for producing the biochemical instrument according to the present invention which comprises coating the surface of a water-insoluble material with the solution containing a polymer represented by formula (I) or (II) and crosslinking the polymer:

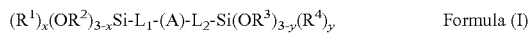   Formula (I)

   Formula (II)

wherein $R^1$ to $R^6$ each independently represent a hydrogen atom or a hydrocarbon group having 8 or fewer carbon atoms; $R^7$ represents a hydrogen atom or a monovalent nonmetal atomic group; x, y, and z each independently represent an integer from 0 to 2; $L^1$ to $L^3$ each independently represent a divalent linking group having 3 or more types of atoms selected from the group consisting of a carbon atom, a hydrogen atom, an oxygen atom, a nitrogen atom, and a sulfur atom; and A and B each independently represent a polymer and an oligomer having structural unit repeats.

Further another aspect of the present invention provides a method for producing the biochemical instrument according to the present invention which comprises coating the surface of a water-insoluble material with the solution containing a polymer represented by formula (III) or (IV) and crosslinking the polymer:

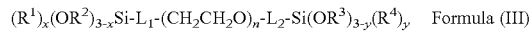   Formula (III)

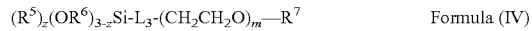   Formula (IV)

N=3 to 25,000; m=3 to 25,000
wherein $R^1$ to $R^6$ each independently represent a hydrogen atom or a hydrocarbon group having 8 or fewer carbon atoms; $R^7$ represents a hydrogen atom or a monovalent nonmetal atomic group; x, y, and z each independently represent an integer from 0 to 2; $L^1$ to $L^3$ each independently represent a divalent linking group having 3 or more types of atoms selected from a carbon atom, a hydrogen atom, an oxygen atom, a nitrogen atom, and a sulfur atom; and A and B each independently represent a polymer and an oligomer having structural unit repeats.

Preferably, crosslinking is carried out by the sol-gel method.

Effect of the Invention

The present invention can provide a biochemical instrument having a surface that can simultaneously inhibit adsorption of a biopolymer and that of a hydrophobic low-molecular-weight compound. According to a preferable embodiment of the present invention, when compounds represented by the formulae (I) and (II) are crosslinked, use of a catalysts accelerates hydrolysis of a metal alkoxide and polycondensation, as compared with general reactions. Accordingly, use of a catalyst enables preparation of a surface with a high crosslinking density and exhibits sufficient effects particularly on inhibition of adsorption of a hydrophobic low-molecular-weight compound, in addition to inhibition of adsorption of a biopolymer. Further, use of a specific catalyst enables setting of a drying temperature for preparing a surface that inhibits nonspecific adsorption at a low level, which in turn enables inhibition of thermal denaturation of a substrate and the like.

BEST MODES FOR CARRYING OUT THE INVENTION

Hereafter, the present invention is described in greater detail.
(1) Biochemical Instrument of the Present Invention The biochemical instrument of the present invention has, on the surface of a water-insoluble material, a region that inhibits adsorption of a hydrophobic low-molecular-weight compound and a region that inhibits adsorption of a biopolymer.

Specific examples of the biochemical instruments of the present invention (e.g., instruments for biochemical assays) include instruments described in pages 13 to 30 of "*Shohokarano baio jikken* (*Basic Bio-experiments*)," (Sankyo Publishing Co., Ltd.). More specific examples include beakers, flasks, petri dishes, pipettes, syringes, centrifuge tubes, needles, tubes, Eppendorf chips, titer plates, micro-flow channels, and filters. It should be noted that the biochemical instruments of the present invention are not limited to those mentioned above and such instruments include any instruments that may be brought into contact with solutions containing biologically-relevant substances (e.g., blood, cells, or proteins) or hydrophobic low-molecular-weight compounds (e.g., pharmaceutical compounds or surfactants).
(2) Water-Insoluble Material that Constitutes Biochemical Instrument Water-insoluble materials that constitute the biochemical instrument of the present invention are not particularly limited. For example, materials that are commonly used for biochemical instruments can be used, and a plastic or glass material can be used. Specific examples of water-insoluble materials include, but are not limited to, polystyrene, polypropylene, acrylic polymer, cycloolefin polymer, polyethylene terephthalate (PET), triacetyl cellulose (TAC), polydimethylsiloxane (PDMS), and fluorine resin. Specific examples of fluorine resins (e.g., Teflon®) include PTFE (polytetrafluoroethylene), PFA (tetrafluoroethylene-perfluoroalkyl vinyl ether copolymer), FEP (tetrafluoroethylene-hexafluoropropyrene copolymer), ETFE (tetrafluoroethylene-ethylene copolymer), PVDF (polyvinylidene fluoride), PCTFE (polychlorotrifluoroethylene), and ECTFE (chlorotrifluoroethylene-ethylene copolymer).

(3) Outline of a Region that Inhibits Adsorption of a Hydrophobic Low-Molecular-Weight Compound and a Region that Inhibits Adsorption of a Biopolymer According to the present invention, a region that inhibits adsorption of a hydrophobic low-molecular-weight compound and a region that inhibits adsorption of a biopolymer are present on the surface of a water-insoluble material. According to a preferable embodiment of the present invention, a region that inhibits adsorption of a biopolymer is located at a position more distant from the surface of a water-insoluble material than a region that inhibits adsorption of a hydrophobic low-molecular-weight compound and/or at a position within the region that inhibits adsorption of a hydrophobic low-molecular-weight compound. According to the present invention, specifically, a region that inhibits adsorption of a hydrophobic low-molecular-weight compound and a region that inhibits adsorption of a biopolymer may be superposed on top of each other. Alternatively, a region that inhibits adsorption of a biopolymer may infiltrate a region that inhibits adsorption of a hydrophobic low-molecular-weight compound to form a hybrid structure (see FIG. 1).

In the present invention, examples of target substances whose adsorption is to be inhibited include those described in *Saibou seibutsugaku jiten* (*Dictionary of cell biology*), Asakura Publishing Co., Ltd., pp. 148 to 149. The term "hydrophobic low-molecular-weight compound" preferably refers to a compound having a molecular weight of 2,000 or smaller, and specific examples thereof include drugs (e.g., medicine, narcotics, or high explosives), surfactants, and lipids. The term "target biopolymer whose adsorption is to be inhibited" in the present invention preferably refers to a polymer having a molecular weight of 5,000 or higher. Specific examples thereof include proteins, antibodies, nucleic acids (DNA and RNA), and polysaccharides.

The term "inhibit (or inhibition)" used herein refers to decrease of the amount of the biopolymer or hydrophobic low-molecular-weight compound to be adsorbed to a water-insoluble material, which has not been subjected to various treatment.

In this description, "the region that inhibits adsorption of a hydrophobic low-molecular-weight compound" may be of any shape, area, and volume, provided that such region has a function of inhibiting adsorption of a hydrophobic low-molecular-weight compound. Similarly, "the region that inhibits adsorption of a biopolymer" may be of any shape, area, and volume, provided that such region has a function of inhibiting adsorption of a biopolymer compound. The coverage of the surface of a water-insoluble material with a region that inhibits adsorption of a hydrophobic low-molecular-weight compound and a region that inhibits adsorption of a biopolymer is preferably 90% or more, further preferably 95% or more, and particularly preferably 100%.

(4) Specific Examples of a Region that Inhibits Adsorption of a Hydrophobic Low-Molecular-Weight Compound In the present invention, specific examples of a region that inhibits adsorption of a hydrophobic low-molecular-weight compound include an inorganic crosslinked polymer and an organic crosslinked polymer, such as a hydrolyzed condensate of a metal alkoxide.

In the present invention, an inorganic crosslinked polymer preferably has a three-dimensionally crosslinked structure of the metal-oxygen bond, such as Ti—O, Si—O, Zr—O, Mn—O, Ce—O, Ba—O, or Al—O. Such inorganic crosslinked polymer is formed by a technique referred to as the sol-gel method in which a metal alkoxide compound is allowed to react with water to convert an alkoxy group contained in the metal alkoxide compound into a hydroxyl group, and a polymer having a hydroxyl metal group obtained via polymerization condensation is subjected to dehydration or dealcoholization to form a covalent bond thereby three dimensionally crosslinking them. An example of metal alkoxides that can be used for the sol-gel method for preparing a region that inhibits adsorption of a hydrophobic low-molecular-weight compound is a compound in which an alkoxy group is a lower alkoxy group, such as a methoxy, ethoxy, isopropoxy, propoxy, isobutoxy, butoxy, or tert-butoxy group. A metal alkoxide that forms the inorganic crosslinked polymer may be a compound in which part of the alkoxy group is substituted with an alkyl group, which may have a functional group, such as a silane coupling agent. Examples of solvents that can be used for the sol-gel method include a polar solvent, such as alcohol (e.g., ethyl alcohol, isopropyl alcohol, or butyl alcohol) and ketone, and various organic solvents, such as hydrocarbon and halogenated hydrocarbon. In order to accelerate the reaction, a metal alkoxide in the solution may be partially hydrolyzed in advance. In order to accelerate hydrolysis, a small amount of water and/or an acid as a hydrolysis catalyst may be added to the solution of a metal alkoxide.

In the present invention, an organic crosslinked polymer is provided in order to inhibit adsorption of a hydrophobic low-molecular-weight compound. Accordingly, such organic crosslinked polymer is preferably prepared via three-dimensional crosslinking of hydrophilic polymers. Hydrophilic polymers can be three-dimensionally crosslinked via conventional techniques. For example, a method comprising three-dimensional crosslinking of polysaccharides using an acid catalyst-based N-alkyloxy crosslinking agent as described in Paragraph Nos. 0033 to 0045 of JP Patent Publication (kokai) No. 2004-314073 (A), a method comprising three-dimensional crosslinking of polyvinyl alcohol using a crosslinking agent as described in Paragraph Nos. 0009 to 0015 of JP Patent Publication (kokai) No. 2000-301837 (A), a method comprising three-dimensional crosslinking of polysaccharides using a crosslinking agent as described in Paragraph Nos. 0011 and 0012 of JP Patent Publication (kokai) No. H-5-230101 (A) (1993), a method of three-dimensional crosslinking via copolymerization of a hydrophilic monomer and a crosslinking unsaturated monomer as described in Paragraph Nos. 0012 to 0043 of JP Patent Publication (kokai) No. H8-120003 (A) (1996), a method of three-dimensional crosslinking via irradiation of n-vinyl carboxylic acid amide and a crosslinking agent with electron beams as described in Paragraph Nos. 0013 to 0020 of JP Patent Publication (kokai) No. 2004-58566 (A), or a method of three-dimensional crosslinking via irradiation of polyvinyl alcohol with electron beams as described in Paragraph Nos. 0006 to 0016 of JP Patent Publication (kokai) No. H9-87395 (A) (1997) can be preferably employed, although methods are not limited thereto.

(5) Region that Inhibits Adsorption of a Biopolymer

A region that inhibits adsorption of a biopolymer is preferably a hydrophilic polymer, and more preferably a non-charged hydrophilic polymer. The term "non-charged" used herein means that the polymer does not have an electric charge that is strong enough to electrostatically suction and/or electrostatically repulse a biopolymer or hydrophobic low-molecular-weight compound. A non-charged hydrophilic polymer may have a weak electric charge that would not provide electrostatic interaction. Specific examples of non-charged hydrophilic polymers include, but are not limited to, polyethylene glycol, polyvinyl pyrrolidone, polyvinyl alcohol, poly(hydroxyalkyl)methacrylate, polyacrylamide, a polymer having a phosphorylcholine group in a side chain, polysaccharide, and polypeptide.

(6) Specific Examples of Region that Inhibits Adsorption of a Hydrophobic Low-Molecular-Weight Compound and Region that Inhibits Adsorption of a Biopolymer In the present invention, specific examples of a region that inhibits adsorption of a hydrophobic low-molecular-weight compound and a region that inhibits adsorption of a biopolymer include those that are obtained by crosslinking the compounds represented by formulae (I) and (II).

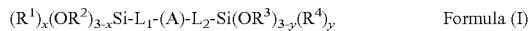

$(R^1)_x(OR^2)_{3-x}Si-L_1-(A)-L_2-Si(OR^3)_{3-y}(R^4)_y$  Formula (I)

$(R^5)_z(OR^6)_{3-z}Si-L_3-(B)-R^7$  Formula (II)

Also, substances obtained by crosslinking the compounds represented by formulae (III) and (IV) can be preferably used.

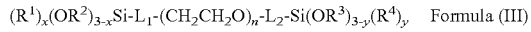

$(R^1)_x(OR^2)_{3-x}Si-L_1-(CH_2CH_2O)_n-L_2-Si(OR^3)_{3-y}(R^4)_y$  Formula (III)

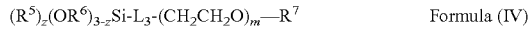

$(R^5)_z(OR^6)_{3-z}Si-L_3-(CH_2CH_2O)_m-R^7$  Formula (IV)

N=3 to 25,000, m=3 to 25,000

In formulae (I), (II), (III), and (IV), $R^1$ to $R^6$ each independently represent a hydrogen atom or a hydrocarbon group having 8 or fewer carbon atoms; $R^7$ represents a hydrogen atom or a monovalent nonmetal atomic group; and x, y, and z each independently represent an integer from 0 to 2. The portions represented by $-Si(OR^2)_{3-x}(R^1)_x$ and $-Si(OR^3)_{3-y}(R^4)_y$ in formulae (I) and (III) and the portion represented by $-Si(OR^6)_{3-z}(R^5)_z$ in formulae (II) and (IV) are polymerized via crosslinking ($OR^2$, $OR^3$, and $OR^5$ are discharged outside the system via hydrolysis and $R^1$, $R^4$, and $R^5$ are crosslinked with Si) to form a region that inhibits adsorption of a hydrophobic low-molecular-weight compound. $L^1$ to $L^3$ each independently represent a divalent linking group having 3 or more types of atoms selected a carbon atom, a hydrogen atom, an oxygen atom, a nitrogen atom, and a sulfur atom.

In formulae (I) and (II), A and B each independently represent a polymer and an oligomer having structural unit repeats.

Examples of hydrocarbon groups represented by $R^1$ to $R^6$ include an alkyl group and an aryl group, with a linear, branched, or cyclic alkyl group having 1 to 8 carbon atoms being preferable. Specific examples include methyl, ethyl, propyl, butyl, pentyl, hexyl, heptyl, octyl, isopropyl, isobutyl, s-butyl, t-butyl, isopentyl, neopentyl, 1-methylbutyl, isohexyl, 2-ethylhexyl, 2-methylhexyl, and cyclopentyl groups.

From the viewpoint of effects and availability, preferably, $R^1$ to $R^6$ each independently represent a hydrogen atom, a methyl group, or an ethyl group.

These hydrocarbons may further be optionally substituted. When an alkyl group is substituted, a substituted alkyl group is constituted via binding of a substituent to an alkylene group, and a monovalent nonmetal atomic group other than hydrogen is used as a substituent. Examples of preferable substituents include a halogen atom (—F, —Br, —Cl, —I) and hydroxyl, alkoxy, aryloxy, mercapto, alkylthio, arylthio, alkyldithio, aryldithio, amino, N-alkylamino, N,N-diarylamino, N-alkyl-N-arylamino, acyloxy, carbamoyloxy, N-alkylcarbamoyloxy, N-arylcarbamoyloxy, N,N-dialkylcarbamoyloxy, N,N-diarylcarbamoyloxy, N-alkyl-N-arylcarbamoyloxy, alkylsulfoxy, arylsulfoxy, acylthio, acylamino, N-alkylacylamino, N-arylacylamino, ureide, N'-alkylureide, N',N'-dialkylureide, N'-arylureide, N',N'-diarylureide, N'-alkyl-N'-arylureide, N-alkylureide, N-arylureide, N'-alkyl-N-alkylureide, N'-alkyl-N-arylureide, N',N'-dialkyl-N-alkylureide, N',N'-dialkyl-N-arylureide, N'-aryl-N-alkylureide, N'-aryl-N-arylureide, N',N'-diaryl-N-alkylureide, N',N'-diaryl-N-arylureide, N'-alkyl-N'-aryl-N-alkylureide, N'-alkyl-N'-aryl-N-arylureide, alkoxycarbonylamino, aryloxycarbonylamino, N-alkyl-N-alkoxycarbonylamino, N-alkyl-N-aryloxycarbonylamino, N-aryl-N-alkoxycarbonylamino, N-aryl-N-aryloxycarbonylamino, formyl, acyl, carboxyl, alkoxycarbonyl, aryloxycarbonyl, carbamoyl, N-alkylcarbamoyl, N,N-dialkylcarbamoyl, N-arylcarbamoyl, N,N-diarylcarbamoyl, N-alkyl-N-arylcarbamoyl, alkylsulfinyl, arylsulfinyl, alkylsulfonyl, arylsulfonyl, sulfo (—SO$_3$H) and a conjugate base group thereof (hereafter referred to as sulfonate), alkoxysulfonyl, aryloxysulfonyl, sulfinamoyl, N-alkylsulfinamoyl, N,N-dialkylsulfinamoyl, N-arylsulfinamoyl, N,N-diarylsulfinamoyl, N-alkyl-N-arylsulfinamoyl, sulfamoyl, N-alkylsulfamoyl, N,N-dialkylsulfamoyl, N-arylsulfamoyl, N,N-diarylsulfamoyl, N-alkyl-N-arylsulfamoylphosphono (—PO$_3$H$_2$) and a conjugate base group thereof (hereafter referred to as phosphonate), dialkylphosphono (—PO$_3$(alkyl)$_2$), diarylphosphono (—PO$_3$(aryl)$_2$), alkylarylphosphono (—PO$_3$(alkyl)(aryl)), monoalkylphosphono (—PO$_3$H(alkyl)) and a conjugate base group thereof (hereafter referred to as alkylphosphonate), monoarylphosphono (—PO$_3$H(aryl)) and a conjugate base group thereof (hereafter referred to as arylphosphonate), phosphonooxy (—OPO$_3$H$_2$) and a conjugate base group thereof (hereafter referred to as phosphonateoxy), dialkylphosphonooxy (—OPO$_3$(alkyl)$_2$), diarylphosphonooxy(—OPO$_3$(aryl)$_2$), alkylarylphosphonooxy (—OPO(alkyl)(aryl)), monoalkylphosphonooxy (—OPO$_3$H(alkyl)) and a conjugate base group thereof (hereafter referred to as alkylphosphonateoxy), monoarylphosphonooxy (—OPO$_3$H(aryl)) and a conjugate base group thereof (hereafter referred to as arylphosphonateoxy), morpholino, cyano, nitro, aryl, alkenyl, and alkynyl groups.

A specific example of alkyl in such substituents is also alkyl that is defined concerning $R^1$ to $R^6$. Specific examples of aryl include phenyl, biphenyl, naphthyl, tolyl, xylyl, mesityl, cumenyl, chlorophenyl, bromophenyl, chloromethylphenyl, hydroxyphenyl, methoxyphenyl, ethoxyphenyl, phenoxyphenyl, acetoxyphenyl, benzoyloxyphenyl, methylthiophenyl, phenylthiophenyl, methylaminophenyl, dimethylaminophenyl, acetylaminophenyl, carboxyphenyl, methoxycarbonylphenyl, ethoxyphenylcarbonyl, phenoxycarbonylphenyl, N-phenylcarbamoylphenyl, phenyl, cyanophenyl, sulfophenyl, sulfonatephenyl, phosphonophenyl, and phosphonatephenyl groups. Examples of alkenyl include vinyl, 1-propenyl, 1-butenyl, cinnamyl, and 2-chloro-1-ethenyl groups, and examples of alkynyl include ethynyl, 1-propynyl, 1-butynyl, and trimethylsilylethynyl groups. Examples of $G^1$ in acyl($G^1$CO—) include hydrogen and the aforementioned alkyl and aryl groups.

Among these substituents, a halogen atom (—F, —Br, —Cl, or —I) and alkoxy, aryloxy, alkylthio, arylthio, N-alkylamino, N,N-dialkylamino, acyloxy, N-alkylcarbamoyloxy, N-arylcarbamoyloxy, acylamino, formyl, acyl, carboxyl, alkoxycarbonyl, aryloxycarbonyl, carbamoyl, N-alkylcarbamoyl, N,N-dialkylcarbamoyl, N-arylcarbamoyl, N-alkyl-N-arylcarbamoyl, sulfo, sulfonate, sulfamoyl, N-alkylsulfamoyl, N,N-dialkylsulfamoyl, N-arylsulfamoyl, N-alkyl-N-arylsulfamoyl, phosphono, phosphonate, dialkylphosphono, diarylphosphono, monoalkylphosphono, alkylphosphonate, monoarylphosphono, arylphosphonate, phosphonooxy, phosphonateoxy, aryl, and alkenyl groups are more preferable.

An example of alkylene in a substituted alkyl group is a group which is obtained by removing any one of the hydrogen atoms of the alkyl group having 1 to 20 carbon atoms so as to prepare a divalent organic residue. Preferable examples include linear alkylene having 1 to 12 carbon atoms, branched alkylene having 3 to 12 carbon atoms, and cyclic alkylene having 5 to 10 carbon atoms. Specific examples of preferable substituted alkyl obtained via combination of such substituent and alkylene include chloromethyl, bromomethyl, 2-chloroethyl, trifluoromethyl, methoxymethyl, methoxyethoxyethyl, allyloxymethyl, phenoxymethyl, methylthiomethyl, tolylthiomethyl, ethylaminoethyl, diethylaminopropyl, morpholinopropyl, acetyloxymethyl, benzoyloxymethyl, N-cyclohexylcarbamoyloxyethyl, N-phenylcarbamoyloxyethyl, acetylaminoethyl, N-methylbenzoylaminopropyl, 2-oxyethyl, 2-oxypropyl, carboxypropyl, methoxycarbonylethyl, allyloxycarbonylbutyl, chlorophenoxycarbonylmethyl, carbamoylmethyl, N-methylcarbamoylethyl, N,N-dipropylcarbamoylmethyl, N-(methoxyphenyl)carbamoylethyl, N-methyl-N-(sulfophenyl)carbamoylmethyl, sulfobutyl, sulfonatebutyl, sulfamoylbutyl, N-ethylsulfamoylmethyl, N,N-dipropylsulfamoylpropyl, N-tolylsulfamoylpropyl, N-methyl-N-(phosphonophenyl)sulfamoyloctyl, phosphonobutyl, phosphonatehexyl, diethylphosphonobutyl, diphenylphosphonopropyl, methylphosphonobutyl, methylphosphonatebutyl, tolylphosphonohexyl, tolylphosphonatehexyl, phosphonooxypropyl, phosphonateoxybutyl, benzyl, phenethyl, α-methylbenzyl, 1-methyl-1-phenylethyl, p-methylbenzyl, cinnamyl, allyl, 1-propenylmethyl, 2-butenyl, 2-methylallyl, 2-methylpropenylmethyl, 2-propynyl, 2-butynyl, and 3-butynyl groups.

x, y, and z each independently represent 0, 1, or 2, with 0 being particularly preferable.

$R^7$ represent a region that inhibits adsorption of a biopolymer, when compounds represented by formulae (I) to (IV) are crosslinked. An example of a monovalent nonmetal atomic group represented by $R^7$ is a monovalent nonmetal atomic group that is listed as a specific example of $R^1$ to $R^6$. Specific examples preferably include methyl, ethyl, propyl, butyl, pentyl, hexyl, heptyl, octyl, isopropyl, isobutyl, s-butyl, t-butyl, isopentyl, neopentyl, 1-methylbutyl, isohexyl, 2-ethylhexyl, 2-methylhexyl, cyclopentyl, a halogen atom, and hydroxyl groups. From the viewpoint of improvement in hydrophilicity and availability, a hydrogen atom, a methyl group, and a hydroxyl group are preferable.

$L^1$ to $L^3$ each independently represent a divalent linking group having 3 or more types of atoms selected from a carbon atom, a hydrogen atom, an oxygen atom, a nitrogen atom, and a sulfur atom. Specifically, such group comprises 1 to 60 carbon atoms, 0 to 10 nitrogen atoms, 0 to 50 oxygen atoms, 1 to 100 hydrogen atoms, and 0 to 20 sulfur atoms. Examples of more specific linking groups include those constituted by the following structural units or combinations of any thereof.

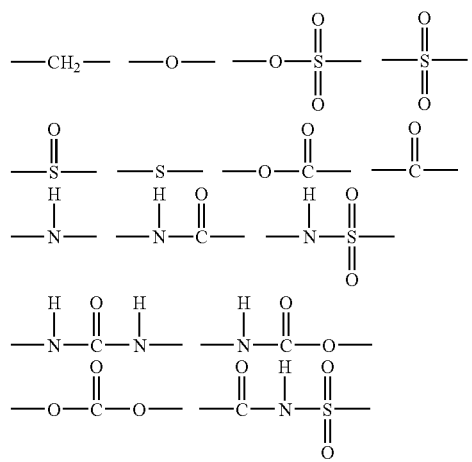

A and B each independently represent a hydrophilic polymer and a hydrophilic oligomer having structural unit repeats, which are regions that inhibit adsorption of a biopolymer. Specifically, it is preferably any of polyethylene glycol, polyvinyl pyrrolidone, polyvinyl alcohol, poly(hydroxyalkyl) methacrylate, polyacrylamide, a polymer having a phosphorylcholine group in a side chain, polysaccharide, or polypeptide.

Such polymer and oligomer may comprise a single type of a structural unit or two or more types of structural units.

The molecular weight of the organosilicon compound represented by any of formulae (I) to (IV) is preferably 100 to 1,000,000, more preferably 400 to 500,000, and most preferably 1,000 to 200,000. In order to bring the molecular weight to such a preferable range, the structure of the alkoxysilyl group at the terminus, the structure and the molar ratio of polymerization of the polymer and the oligomer represented by A and B, and the number of instances of polymerization may be determined.

In the present invention, examples of particularly preferable compounds represented by formula (III) include polymers represented by formulae below:

Polymer 1

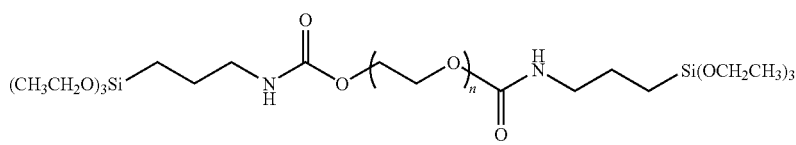

Polymer 2
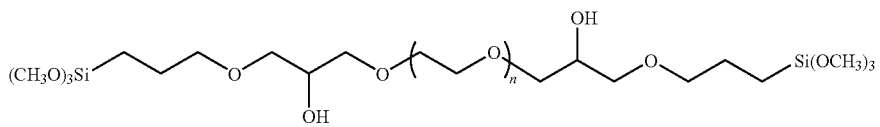

Polymer 3
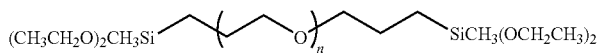

wherein n represents an integer from 3 to 25,000.

In the present invention, examples of particularly preferable compounds represented by formula (IV) include polymers represented by formulae below:

Polymer 4
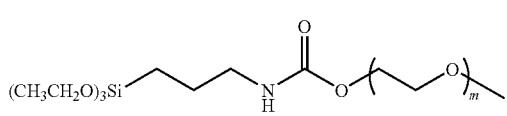

Polymer 5
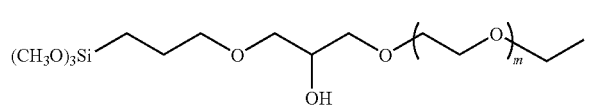

Polymer 6
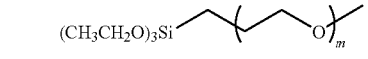

wherein m represents an integer from 3 to 25,000.

In the present invention, examples of particularly preferable compounds represented by formula (IV) include polymers represented by the formula representing Polymer 4.

(7) Catalyst Used when a Solution Containing Polymers Represented by formulae (I) to (IV) is Coated and the Polymer is Crosslinked In the present invention, a catalyst can be used when coating the surface of a water-insoluble material with a solution containing the polymer represented by formula (I) or (II) or the polymer represented by formulae (III) or (IV) for crosslinking. Examples of catalysts that can be used herein include hydrogen halide such as hydrochloric acid, nitric acid, sulfuric acid, sulfurous acid, hydrogen sulfide, perchloric acid, hydrogen peroxide, carbonic acid, carboxylic acids such as formic acid or acetic acid, substituted carboxylic acid represented by a structural formula: RCOOH in which R has been substituted with the other element or substituent, a compound exhibiting acidity such as sulfonic acid (e.g., benzenesulfonic acid), ammoniacal base such as aqueous ammonia, and a basic compound (e.g., an amine, such as ethylamine or aniline). A Lewis acid catalyst comprising a metal complex can be preferably used. A particularly preferable catalyst is a metal complex catalyst that is composed of a metal element selected from Groups 2A, 3B, 4A, and 5A of the periodic table, and oxo or hydroxyl acid-containing compounds selected from among β-diketone, ketoester, hydroxycarboxylic acid or ester thereof, amino alcohol and an enolic active hydrogen compound.

Among the constitutional metal elements, elements of Group 2A, such as Mg, Ca, Sr, and Ba, elements of Group 3B, such as Al and Ga, elements of Group 4A, such as Ti and Zr, and elements of Group 5A, such as V, Nb, and Ta, are preferable, and such elements form complexes having excellent catalytic effects. Among such complexes, complexes obtained from Si, Zr, Al, and Ti are excellent and preferable.

Examples of oxo or hydroxyl acid-containing compounds that constitute ligands of the metal complex used in the present invention include β-diketone such as acetylacetone, acetylacetone (2,4-pentanedione) and 2,4-heptadione; ketoesters such as methyl acetoacetate, ethyl acetoacetate, and butyl acetoacetate; hydroxycarboxylic acids and ester thereof such as lactic acid, methyl lactate, salicylic acid, ethyl salicylate, phenyl salicylate, malic acid, tartaric acid, and methyl tartrate; ketoalcohols such as 4-hydroxy-4-methyl-2-pentanone, 4-hydroxy-2-pentanone, 4-hydroxy-4-methyl-2-pentanone and 4-hydroxy-2-heptanone; amino alcohols such as monoethanolamine, N,N-dimethylethanolamine, N-methyl-monoethanolamine, diethanolamine and triethanolamine; enolic active compounds such as methylolmelamine, methylol urea, methylolacrylamide and malonic acid diethyl ester; and a compound having a substituent on methyl group, methylene group or carbonylcarbon of acetylacetone (2,4-pentanedione).

A preferable ligand is an acetylacetone derivative, and the term "acetylacetone derivative" used in the present invention refers to a compound having a substituent on methyl group, methylene group or carbonylcarbon of acetylacetone. Groups to be substituted on methyl of acetylacetone are linear or branched alkyl, acyl, hydroxyalkyl, carboxyalkyl, alkoxy, or alkoxyalkyl having 1 to 3 carbon atoms. Groups to be substituted on methylene of acetylacetone are carboxyl groups, linear or branched carboxyalkyl or hydroxyalkyl having 1 to 3 carbon atoms. A substituent to be substituted on carbonyl carbon of acetylacetone is alkyl having 1 to 3 carbon atoms. In such a case, a hydrogen atom is added to carbonyl oxygen to become a hydroxyl group.

Specific examples of preferable acetylacetone derivatives include acetylacetone, ethylcarbonylacetone, n-propylcarbonylacetone, i-propylcarbonylacetone, diacetylacetone, 1-acetyl-1-propionyl-acetylacetone, hydroxyethylcarbonylacetone, hydroxypropylcarbonylacetone, acetoacetic acid, acetopropionic acid, diacetoacetic acid, 3,3-diacetopropionic acid, 4,4-diacetobutyric acid, carboxyethylcarbonylacetone, carboxypropylcarbonylacetone, and diacetone alcohol. Acetylacetone and diacetylacetone are particularly preferable. The complex of the acetylacetone derivative and the metal element is a mononuclear complex having 1 to 4 molecules of acetylacetone derivatives coordinated per metal element. When the valence of the metal element is greater than a total valence of the acetylacetone derivative, ligands that are commonly used for common ligands, such as water molecules, halogen ions, nitro groups, or ammonia groups, may be coordinated.

Examples of preferable metal complexes include tris (acetylacetonate)aluminum complex salt, di(acetylacetonate)aluminum.aquo complex salt, mono(acetylacetonate) aluminum.chloro complex salt, di(diacetylacetonate)

aluminum complex salt, ethyl acetoacetate aluminum diisopropylate, aluminum tris(ethyl acetoacetate), cyclic aluminum oxide propylate, tris(acetylacetonate)balium complex salt, di(acetylacetonate)titanium complex salt, tris(acetylacetonate)titanium complex salt, di-i-propoxy-bis(acetylacetonate)titanium complex salt, zirconium tris(ethyl acetoacetate), and zirconium tris(benzoic acid) complex salt. These complexes are excellent in terms of stability in aqueous coating solutions and the effects of accelerating gelation in the sol-gel reaction at the time of heat-drying. Ethyl acetoacetate aluminum diisopropylate, aluminum tris(ethyl acetoacetate), di(acetylacetonate)titanium complex salt, and zirconium tris (ethyl acetoacetate) are particularly preferable.

The description concerning counter salts of the metal complex is omitted herein. A type of a counter salt is not limited, provided that it is a water-soluble salt that retains charge neutrality as the complex compound. For example, salt retaining stoichiometric neutrality, such as nitrate, halogen acid salt, sulfate, or phosphate, is used. Behavior of metal complexes in the silica sol-gel reaction is described in detail in J. Sol-Gel. Sci. and Tec. 16. 209, 1999. The scheme shown below is deduced as a reaction mechanism. In the reaction solution, specifically, a metal complex is stable while maintaining a coordination structure. In the dehydration-condensation reaction that begins with a process of heat drying following coating of the reaction solution, crosslinking is considered to be promoted by a mechanism similar to that of an acid catalyst. In any cases, use of the metal complex has led to satisfactory improvement in terms of temporal stability of the reaction solution, quality of the surface that inhibits nonspecific adsorption, high capacity, and high durability.

(8) Improvement in Adhesion between a Water-Insoluble Material and a Region that Inhibits Adsorption of a Hydrophobic Low-Molecular-Weight Compound and a Region that Inhibits Adsorption of a Biopolymer In the present invention, either or both surfaces of a water-insoluble material can be hydrophilized via the oxidation method, a surface-roughening method, or other means, according to need, in order to improve adhesion between a water-insoluble material and a region that inhibits adsorption of a hydrophobic low-molecular-weight compound and a region that inhibits adsorption of a biopolymer. Examples of the oxidation method include corona discharge, glow discharge, chromic acid treatment (wet treatment), flame treatment, hot-air treatment, and ozone/ultraviolet radiation. As a surface-roughening method, a surface can be mechanically roughened via sandblasting, brush polishing, or other means.

As the other method for further improving adhesion, one or more adhesive layer can be provided. As materials for such adhesive layer, hydrophilic resin, water-dispersible latex, and the like can be used.

Examples of hydrophilic resin include polyvinyl alcohol (PVA), cellulosic resins (e.g., methylcellulose (MC), hydroxyethylcellulose (HEC), and carboxymethylcellulose (CMC)), chitin, chitosan, starch, resin having an ether bond (e.g., polyethylene glycol (PEG) or polyvinyl ether (PVE)), and resin having a carbamoyl group (e.g., polyacrylamide (PAAM) or polyvinyl pyrrolidone (PVP)). Also, carboxyl-containing polyacrylate, maleic acid resin, alginate, and gelatin can also be used.

Among them, at least one resin selected from among polyvinyl alcohol resin, cellulose resin, resin having an ether bond, carbamoyl-containing resin, carboxyl-containing resin, and gelatin is preferable, with polyvinyl alcohol (PVA) resin and gelatin being particularly preferable.

Examples of water-dispersible latex include acrylic latex, polyester latex, NBR resin, polyurethane latex, polyvinyl acetate latex, SBR resin, and polyamide latex. Acrylic latex is particularly preferable.

The hydrophilic resin and the water-dispersible latex may be used alone or in combinations of two or more. Hydrophilic resin may be used in combination with water-dispersible latex.

A crosslinking agent for crosslinking the hydrophilic resin or the water-dispersible latex may be used.

A conventional crosslinking agent that thermally realizes crosslinking can be used in the present invention. A general thermal crosslinking agent is described in, for example, "*Kakyouzai (crosslinking agent) Handbook*," Shinzo Yamashita and Tosuke Kaneko, Taiseisha Ltd., 1981. The number of functional groups of the crosslinking agent to be used in the present invention is not particularly limited, provided that such number is two or more and such functional groups can effectively crosslink with the hydrophilic resin or water-dispersible latex. Specific examples of thermal crosslinking agents include: polycarboxylic acid, such as polyacrylic acid; amine compounds, such as polyethyleneimine; polyepoxy compounds, such as ethylene or propylene glycol diglycidyl ether, tetraethylene glycol diglycidyl ether, nonaethylene glycol diglycidyl ether, polyethylene or polypropylene glycol glycidyl ether, neopentyl glycol diglycidyl ether, 1,6-hexanediol diglycidyl ether, trimethylolpropane triglycidyl ether, and sorbitol polyglycidyl ether; polyaldehyde compounds, such as glyoxal and terephthalic aldehyde; polyisocyanate compounds, such as tolylene diisocyanate, hexamethylene diisocyanate, diphenylmethane isocyanate, xylinene diisocyanate, polymethylene polyphenyl isocyanate, cyclohexyl diisocyanate, cyclohexane phenylene diisocyanate, naphthalene-1,5-diisocyanate, isopropylbenzene-2,4-diisocyanate, and polypropylene glycol/tolylene diisocyanate adduct; block polyisocyanate compounds; silane coupling agents, such as tetraalkoxysilane; metallic crosslinking agents, such as acetylacetonate of aluminum, copper, and iron (III); and polymethylol compounds, such as trimethylolmelamine and pentaerythritol. Among these thermal crosslinking agents, water soluble crosslinking agents are preferable from the viewpoint of ease of preparation of a coating solution and prevention of lowering in hydrophilicity of the prepared hydrophilic layer.

The total amount of the hydrophilic resin and/or water-dispersible latex in the adhesion layer is preferably 0.01 to 20 g/m$^2$, and more preferably 0.1 to 10 g/m$^2$.

As an adhesion layer, preferably, a resultant of hydrolysis and polycondensation of a composition comprising at least a metal alkoxide compound and the catalyst used for forming the surface that inhibits nonspecific adsorption described above (i.e., a catalyst used for crosslinking via coating of a solution containing the polymer represented by any of formulae (I) to (IV)) can be used. As a metal alkoxide compound used for forming an adhesion layer, a alkoxide compound of metal selected from among Si, Ti, Zr, Al, Mn, Ce, and Ba is particularly preferable.

The adhesion layer resulting from hydrolysis and polycondensation of a composition comprising at least a metal alkoxide compound and the catalyst used for forming a surface that inhibits nonspecific adsorption described above has a crosslinked structure.

A metal alkoxide compound that can be used for forming an adhesion layer (hereafter such compound may also be referred to as "metal alkoxide") is a hydrolytically polymerizable compound that has a hydrolytically polycondensable functional group and serves as a crosslinking agent, and such compound forms a strongly crosslinked film resulting from polycondensation of metal alkoxides. Metal alkoxides that can be used for forming an adhesion layer can be represented by formula (V-1) and formula (V-2). In the formulae, $R^8$ represents a hydrogen atom, an alkyl group, or an aryl group; $R^9$ represents an alkyl or aryl group; Z represents Si, Ti or Zr, Mn, Ce, or Ba; and m represents an integer from 0 to 2. When $R^8$ and $R^9$ represent alkyl, the number of carbon atoms is preferably 1 to 4. Alkyl or aryl may optionally have a substituent, and examples of substituents that can be introduced include a halogen atom, an amino group, and a mercapto group. Such compound is a low-molecular-weight compound preferably having a molecular weight of 2,000 or smaller.

(V-1)

(V-2)

Specific examples of hydrolyzable compounds represented by formulae (V-1) and (V-2) are demonstrated below, although the compounds of the present invention are not limited thereto. When Z is Si, specifically, examples of silicon-containing hydrolyzable compounds include trimethoxysilane, tetramethoxysilane, tetraethoxysilane, tetrapropoxysilane, methyltrimethoxysilane, dimethyldimethoxysilane, γ-chloropropyltriethoxysilane, γ-mercaptopropyltrimethoxysilane, γ-aminopropyltriethoxysilane, phenyltrimethoxysilane, and diphenyldimethoxysilane. Among these compounds, trimethoxysilane, tetramethoxysilane, tetraethoxysilane, methyltrimethoxysilane, dimethyldimethoxysilane, phenyltrimethoxysilane, and the like are particularly preferable.

When Z is Ti, specifically, examples of titanium-containing hydrolyzable compounds include trimethoxy titanate, tetramethoxy titanate, triethoxy titanate, tetraethoxy titanate, tetrapropoxy titanate, chlorotrimethoxy titanate, chlorotriethoxy titanate, ethyltrimethoxy titanate, methyltriethoxy titanate, ethyltriethoxy titanate, diethyl diethoxy titanate, phenyltrimethoxy titanate, and phenyltriethoxy titanate. When Z is Zr, specifically, an example of zirconium-containing hydrolysable compounds is zirconate corresponding to the compound exemplified as the titanium-containing compound above.

When a central metal is Al, specifically, examples of aluminum-containing hydrolyzable compounds include trimethoxy aluminate, triethoxy aluminate, tripropoxy aluminate, and triisopropoxy aluminate.

Among metal alkoxides, use of Si alkoxide is particularly preferable from the viewpoint of reactivity and availability.
(9) Applications of Biochemical Instrument of the Present Invention The biochemical instrument of the present invention can be used as a member for constituting a biosensor (e.g., a detector plane or a flow channel).

The term "biosensor" is understood in the most extensive sense, and the term refers to a sensor that converts an interaction between biomolecules into a signal such as an electric signal to assay and detect the target substance. A conventional biosensor is composed of a receptor site that recognizes a chemical substance as a target of detection and a transducer site that converts the resulting physical or chemical change into an electric signal. Substances having an affinity with each other, such as enzyme/substrate, enzyme/coenzyme, antigen/antibody, and hormone/receptor, are present in a living body. The biosensor operates on the principle such that one of the substances having an affinity with each other, as described above, is immobilized on a substrate to be used as a molecule-recognizing substance, so that the other substance can be selectively assayed.

In the biosensor, metal surface or metal film can be used as a substrate. A metal that constitutes a metal surface or metal film is not particularly limited, provided that surface plasmon resonance can be generated in the case of the use of such metal surface or film for a surface plasmon resonance biosensor, for example. Preferable examples include free-electron metals such as gold, silver, copper, aluminum, and platinum, with gold being particularly preferable. Such metal can be used alone or in combination. From the viewpoint of adhesion to the substrate, an interstitial layer comprising chrome or the like may be provided between the substrate and a metal layer.

The thickness of a metal film is not limited. When such metal film is used for a surface plasmon resonance biosensor, for example, the thickness is preferably 0.1 nm to 500 nm, and particularly preferably 1 nm to 200 nm. If the thickness exceeds 500 nm, a surface plasmon phenomenon of media cannot be sufficiently detected. When an interstitial layer comprising chrome or the like is provided, the thickness of such interstitial layer is preferably 0.1 nm to 10 nm.

A metal film can be formed in accordance with conventional techniques. Examples of such techniques include sputtering, vapor deposition, ion plating, electroplating, and electroless plating.

A metal film is preferably provided on a substrate. The term "provided on a substrate" used herein refers to provision of a metal film in direct contact with the substrate and provision thereof via the other layer without a direct contact with the substrate. When a substrate used in the present invention is used for a surface plasmon resonance biosensor, examples of such substrates generally include optical glass, such as BK7, or synthetic resin, and specifically a substrate composed of a material transparent to laser beams, such as polymethyl methacrylate, polyethylene terephthalate, polycarbonate, and cycloolefin polymer. Such substrate is preferably composed of a material that is not anisotropic with regard to polarized light and has excellent workability.

As described above, the biochemical instrument provided by the present invention can be used for a biosensor as a surface that inhibits nonspecific adsorption. For example, such biochemical instrument can be used for a biosensor that retains a waveguide structure on the substrate surface and detects changes in refractive indexes using the waveguide. An assay technique of detecting changes in refractive indexes using the waveguide comprises detection of changes in effective refractive indexes of media located adjacent to the waveguide in terms of optical changes. For example, a site to which such medium is to be supplied has a well structure having a lateral side and a substrate surface of the waveguide structure. Provision of the surface that inhibits nonspecific adsorption of the present invention exclusively on the lateral side of the well structure enables inhibition of nonspecific adsorption of the target analyte to the lateral side of the well structure. This can also prevent the concentration of the target analytes from being diluted. Thus, detection sensitivity of the sensor can be improved. As a means of using a surface that inhibits nonspecific adsorption exclusively to the lateral side of the well structure, the surface that inhibits nonspecific adsorption of the present invention may be provided on the entire inner surface of the well structure, the lateral surface may be covered with a photomask, the well structure may be irradiated with a 500 W supervoltage mercury lamp for 2 hours, and the surface that inhibits nonspecific adsorption of the UV-irradiated region may then be removed. The construction of such biosensor is described in, for example, line 31 of column 6, to line 47 of column 7 and FIGS. 9A and 9B of U.S. Pat. No. 6,829,073.

The present invention is described in greater detail with reference to the following examples, although the technical scope of the present invention is not limited thereto.

Examples

Example 1

This example concerns adsorbing properties of proteins and hydrophobic low-molecular-weight compounds to various types of substrates.
(Preparation of Sample 1)
PMMA (VH, Mitsubishi Chemical Corporation) was subjected to melt-molding to prepare Sample 1.
(Preparation of Sample 2)
Polycarbonate (AD5503, Teijin Limited) was subjected to melt-molding to prepare Sample 2.
(Preparation of Sample 3)
Zeonex (330R, Zeon Corporation) was subjected to melt-molding to prepare Sample 3.
(Preparation of Sample 4)
A glass slide (S-1112, Matsunami Glass Ind., Ltd.) was used.
(Evaluation of Adsorbing Properties)
An aqueous solution of avidin FITC (5 μl, 0.25 mg/ml, pH 5.0, acetate), which is a fluorescent protein, or a solution of hydrophobic compound 1 in methanol (1 μl, concentration: 0.6%) was added dropwise to Samples 1 to 4, and the resultants were allowed to stand at room temperature for 5 minutes, followed by washing with ultrapure water. The fluorescent intensity of the washed sample surface was assayed using FLA8000 (Fuji Photo film) at a detection wavelength of 473 nm, using a filter 530DF20, at a resolution of 20 μm, and with a scan mode of 400 mm/s. The value obtained by subtracting the background fluorescent intensity was designated as an indicator for adsorption. The obtained results are shown in Table 1.

TABLE 1

1

[structure of Compound 1: indole/oxazole cyanine dye with C$_2$H$_5$ groups, (CH$_2$)$_2$SO$_3^-$ substituents, and C$_2$H$_5$—N$^+$ pyridinium counterion]

| | Avidin-FITC | Compound 1 | Remarks |
|---|---|---|---|
| Sample 1 | 751 | 1595792 | Comparative Example |
| Sample 2 | 15425 | 1590507 | Comparative Example |
| Sample 3 | 9534 | 3043 | Comparative Example |
| Sample 4 | 8818 | 107 | Comparative Example |

The amount of the Avidin-FITC protein adsorbed to Sample 1 (i.e., PMMA) was small; however, the amount of the hydrophobic compound 1 adsorbed thereto was very large. The amounts of Avidin-FITC and the hydrophobic compound 1 adsorbed to Sample 2 (i.e., polycarbonate) were very large. The amount of the hydrophobic compound 1 adsorbed to Sample 3 (i.e., a cycloolefin polymer (Zeonex)), was small; however, the amount of Avidin-FITC adsorbed thereto was very large. The amount of the hydrophobic compound 1 adsorbed to Sample 4 (i.e., a glass) was small; however, the amount of Avidin-FITC adsorbed thereto was very large, as in the case of Sample 3. Thus, all samples were found to be insufficient as the surfaces that inhibit adsorption because adsorption of either or both protein or hydrophobic low-molecular-weight compound was strong.

Example 2

This example concerns adsorbing properties of proteins and hydrophobic low-molecular-weight compounds, when a region that inhibits adsorption of a hydrophobic low-molecular-weight compound and a region that inhibits adsorption of a biopolymer of the present invention are provided on a glass.
(Preparation of Sample 5)
Solution A:
Solution A: Ethanol (54.9 g), acetylacetone (2.46 g), and tetraethoxy titanium (2.82 g) were added to a 100-ml beaker, the mixture was agitated at room temperature for 10 minutes, 0.45 g of ultrapure water was added thereto, and the resultant was agitated at room temperature for an additional 60 minutes to prepare a catalyst solution.

Solution B: Ultrapure water (44.12 g) and Polymer 7 (n=31, 1.73 g) were added to a 100-ml beaker, the mixture was agitated to dissolve the polymer therein, and Solution A (10.10 g) and tetramethoxysilane (5.20 g) were added, followed by agitation.

Ultrapure water (1.0 g) was added to Solution B (3.23 g), the mixture was agitated, and the resultant was designated as a coating solution. The coating solution (300 μl) was added dropwise to a glass slide, and the resultant was subjected to spin-coating at 300 rpm for 5 seconds and then at 7,000 rpm for 20 seconds, followed by heating at 100° C. for 10 minutes. Thus, Sample 5 was obtained.

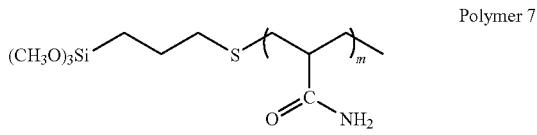

Polymer 7

(Preparation of Sample 6)
Sample 6 was obtained in the same manner as in the case of Sample 5, except that Polymer 7 (m=31) was replaced with Polymer 4 (m=90).

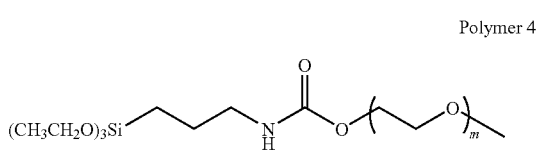

Polymer 4

(Evaluation of Adsorbing Properties)
Sample 5 and Sample 6 were subjected to the same evaluation as in Example 1 to evaluate adsorbing properties of fluorescent protein (avidin-FITC) and hydrophobic compound 1. The obtained results are shown in Table 2.

TABLE 2

|  | Avidin-FITC | Compound 1 | Remarks |
| --- | --- | --- | --- |
| Sample 5 | 6632 | 53 | Present invention |
| Sample 6 | 17 | 386 | Present invention |

Sample 5 having a surface modified with an organic/inorganic complex comprising Polymer 7 (i.e., a polyacrylamide derivative) and silica showed decrease in the amount of proteins adsorbed, compared with Sample 4 (i.e., an unmodified glass). Also, Sample 6 having a surface modified with an organic/inorganic complex comprising Polymer 4 (i.e., a polyethylene glycol derivative) and silica was verified to be capable of very effectively inhibiting adsorption of a protein and a hydrophobic low-molecular-weight compound.

Example 3

This example concerns adsorbing properties of proteins and hydrophobic low-molecular-weight compounds to a surface prepared by forming a thin $SiO_2$ layer as an adhesion layer on a plastic surface and then forming a region that inhibits adsorption of a hydrophobic low-molecular-weight compound and a region that inhibits adsorption of a biopolymer of the present invention thereon.
(Preparation of Sample 7)

Sample 1 was subjected to vacuum deposition with SiO under an oxygen atmosphere to form a 100-nm $SiO_2$ film. Further, Sample 7 was obtained in the same manner as in the case of Sample 6.
(Preparation of Sample 8)

Sample 8 was obtained in the same manner as in the case of Sample 7, except that Sample 1 was replaced with Sample 2.
(Preparation of Sample 9)

Sample 9 was obtained in the same manner as in the case of Sample 7, except that Sample 1 was replaced with Sample 3.
(Evaluation of Adsorbing Properties)

Samples 7 to 9 were subjected to the same evaluation as in Example 1 to evaluate adsorbing properties of fluorescent protein (avidin-FITC) and hydrophobic compound 1. The obtained results are shown in Table 3.

TABLE 3

|  | Avidin-FITC | Compound 1 | Remarks |
| --- | --- | --- | --- |
| Sample 7 | 29 | 449 | Present invention |
| Sample 8 | 0 | 490 | Present invention |
| Sample 9 | 78 | 100 | Present invention |

A hydrophobic plastic surface was covered with a thin $SiO_2$ layer. This demonstrated that the region that inhibits adsorption of a hydrophobic low-molecular-weight compound and the region that inhibits adsorption of a biopolymer of the present invention could be provided on the hydrophobic plastic surface. Further, the region that inhibits adsorption of a hydrophobic low-molecular-weight compound and the region that inhibits adsorption of a biopolymer prepared with the use of Polymer 4 (i.e., a polyethylene glycol derivative) were found to be capable of very effectively inhibiting adsorption of a protein and a hydrophobic low-molecular-weight compound.

The present invention demonstrated that a surface that can very effectively inhibit adsorption of a protein and a hydrophobic low-molecular-weight compound could be provided on a hydrophobic plastic.

Example 4

This example concerns adsorbing properties of proteins and hydrophobic low-molecular-weight compounds to surfaces modified with an MPC polymer and PMEA, which are conventional representative inhibitors of nonspecific adsorption.
(Preparation of Sample 10)

A solution of the MPC polymer in ethanol, i.e., MPC-U (AI Bio Chips Co., Ltd.), was added in an amount of 200 μl dropwise to Sample 1 (i.e., PMMA) and the resultant was subjected to spin-coating at 1,000 rpm for 45 seconds. This operation was repeated 3 times, the resultant was dried at room temperature for 20 minutes in a wet box containing an adequate amount of ethanol, and ultrapure water was brought into contact with the surface for 60 minutes to obtain Sample 10.
(Preparation of Sample 11)

A solution of PMEA (Scientific Polymer Products) in 2% toluene was added in an amount of 200 μl dropwise to Sample 1, and the resultant was subjected to spin-coating at 1,000 rpm for 45 seconds. This operation was repeated 3 times to obtain Sample 11.
(Evaluation of Adsorbing Properties)

Samples 10 and 11 were subjected to the same evaluation as in Example 1 to evaluate adsorbing properties of fluorescent protein (avidin-FITC) and hydrophobic compound 1. The obtained results are summarized in Table 4 together with the results of Sample 1 (unmodified PMMA) and Sample 7 (PMMA subjected to surface modification of the present invention).

TABLE 4

|  | Avidin-FITC | Compound 1 | Remarks |
| --- | --- | --- | --- |
| Sample 1 | 751 | 1595792 | Comparative Example |
| Sample 7 | 29 | 449 | Present invention |
| Sample 10 | 186 | 229473 | Comparative Example |
| Sample 11 | 379 | 1052152 | Comparative Example |

Sample 7 (the present invention) is capable of very effective inhibition of adsorption of a protein and a hydrophobic low-molecular-weight compound. However, Sample 10 modified with an MPC polymer and Sample 11 modified with PMEA were found to have functions of inhibiting adsorption of a protein but have the insufficient capacity for inhibiting adsorption of a hydrophobic low-molecular-weight compound.

Example 5

This example concerns adsorbing properties of a protein and a hydrophobic low-molecular-weight compound, when metal complex catalysts used for forming the region that inhibits adsorption of a hydrophobic low-molecular-weight compound and the region that inhibits adsorption of a biopolymer of the present invention on a glass are changed.
(Preparation of Samples 12 and 13)

Sample 12 and Sample 13 were prepared by forming a layer on a glass in the same manner as in the case of Sample 5 of Example 2, except that the catalysts used for Solution A of Example 2 were replaced with catalysts shown below. Sample 5 and Sample 6 were subjected to the same evaluation as in Example 1 to evaluate adsorbing properties of fluorescent protein (avidin-FITC) and hydrophobic compound 1. The obtained results are shown in Table 5.

Catalyst Used for Sample 12: Aluminate Compound

A solution comprising 10 parts of ethyl acetoacetate aluminum diisopropylate (ALCH, Kawaken Fine Chemicals Co., Ltd.) and 90 parts of ethanol was added to a 200-ml beaker, and the mixture was agitated at room temperature for 30 minutes.

Catalyst Used for Sample 13: Zirconium Chelate Compound

Tetrabutoxy zirconium (50 parts) and acetoacetic acid ethyl (20 parts) were added to a reactor equipped with an agitator, and the mixture was agitated at room temperature for 1 hour to obtain a zirconium chelate compound.

TABLE 5

|  | Avidin-FITC | Compound 1 | Remarks |
|---|---|---|---|
| Sample 12 | 730 | 30 | Present invention |
| Sample 13 | 320 | 20 | Present invention |

(Preparation of Sample 14)
Catalyst Used for Sample 13: 1N Nitric Acid

Ultrapure water (44.12 g) and Polymer 7 (m=31, 1.73 g) were added to a 100-ml beaker, the mixture was agitated to dissolve the polymer therein, and 1N nitric acid (0.50 g) and tetramethoxysilane (5.20 g) were added thereto, followed by agitation. Ultrapure water (1.0 g) was added thereto, the mixture was agitated, and the resultant was designated as a coating solution. The coating solution (300 μl) was added dropwise to a glass slide, and the resultant was subjected to spin-coating at 300 rpm for 5 seconds and then at 7,000 rpm for 20 seconds, followed by heating at 100° C. for 10 minutes. Thus, Sample 14 was obtained.

Sample 14 was subjected to the same evaluation as in Example 1 to evaluate adsorbing properties of fluorescent protein (avidin-FITC) and hydrophobic compound 1. The obtained results are shown in Table 6.

TABLE 6

|  | Avidin-FITC | Compound 1 | Remarks |
|---|---|---|---|
| Sample 14 | 6850 | 85 | Present invention |

Use of catalysts when providing the region that inhibits adsorption of a hydrophobic low-molecular-weight compound and the region that inhibits adsorption of a biopolymer of the present invention was found to realize very effective inhibition of adsorption of a protein and a hydrophobic low-molecular-weight compound.

INDUSTRIAL APPLICABILITY

The biochemical instrument of the present invention is useful particularly in the field of biochemistry, since such instrument has a surface that can simultaneously inhibit adsorption of a biopolymer and that of a hydrophobic low-molecular-weight compound.

BRIEF DESCRIPTION OF THE DRAWING

FIG. 1 is a pattern diagram showing a hybrid structure resulting from infiltration of the region that inhibits adsorption of a biopolymer into the region that inhibits adsorption of a hydrophobic low-molecular-weight compound.

The invention claimed is:

1. A biochemical instrument comprising, on the surface of a water-insoluble material, a region that inhibits adsorption of a hydrophobic low-molecular-weight compound and a region that inhibits adsorption of a biopolymer, wherein
the region that inhibits adsorption of a hydrophobic low-molecular-weight compound has a three-dimensionally crosslinked structure, and
the region that inhibits adsorption of a hydrophobic low-molecular-weight compound and the region that inhibits adsorption of a biopolymer comprise a structure represented by the formula below:

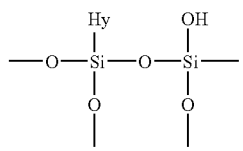

wherein Hy represents a polyethylene glycol, a polyvinyl pyrrolidone, a polyvinyl alcohol, a poly(hydroxyalkyl) methacrylate, a polyacrylamide, a polymer having a phosphorylcholine group in a side chain, a polysaccharide or a polypeptide.

2. The biochemical instrument according to claim 1, wherein the coverage of the surface of a water-insoluble material with the region that inhibits adsorption of a hydrophobic low-molecular-weight compound and the region that inhibits adsorption of a biopolymer is 90% or more.

3. The biochemical instrument according to claim 1, wherein the water-insoluble material is plastic.

4. The biochemical instrument according to claim 1, wherein the water-insoluble material is any of polystyrene, polypropylene, acrylic polymer, cycloolefin polymer, polyethylene terephthalate (PET), triacetyl cellulose (TAC), polydimethylsiloxane (PDMS), or a fluorine resin.

5. The biochemical instrument according to claim 1, wherein an adhesion layer is provided between the water-insoluble material, and the region that inhibits adsorption of a hydrophobic, low-molecular-weight compound and the region that inhibits adsorption of a biopolymer.

6. The biochemical instrument according to claim 1, which is obtained by coating the surface of the water-insoluble material with a solution containing a polymer represented by formula (I) or (II) and crosslinking the polymer:

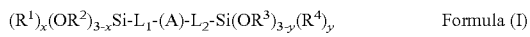

wherein $R^1$ to $R^6$ each independently represents a hydrogen atom or a hydrocarbon group having 8 or fewer carbon atoms; $R^7$ represents a hydrogen atom or a monovalent nonmetal atomic group; x, y, and z each independently represents an integer from 0 to 2; $L^1$ to $L^3$ each independently represents a divalent linking group having 3 or more types of atoms selected from the group consisting of a carbon atom, a hydrogen atom, an oxygen atom, a nitrogen atom, and a sulfur atom; and A and B each independently represents a polymer and an oligomer having structural unit repeats.

7. The biochemical instrument according to claim 1, which is obtained by coating the surface of the water-insoluble material with a solution containing a polymer represented by formula (III) or (IV) and crosslinking the polymer:

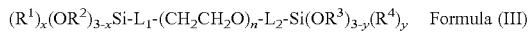

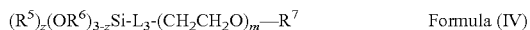

n=3 to 25,000; m=3 to 25,000 wherein $R^1$ to $R^6$ each independently represents a hydrogen atom or a hydrocarbon group having 8 or fewer carbon atoms; $R^7$ represents a hydrogen atom or a monovalent nonmetal atomic group; x, y, and z each independently represents an integer from 0 to 2; and $L^1$ to $L^3$ each independently represents a divalent linking group having 3 or more types of atoms selected from a carbon atom, a hydrogen atom, an oxygen atom, a nitrogen atom, and a sulfur atom.

8. The biochemical instrument according to claim 6, wherein crosslinking is carried out by the sol-gel method.

9. A biosensor comprising the biochemical instrument according to claim 1.

10. A method for producing the biochemical instrument according to claim 1 which comprises coating the surface of a water-insoluble material with a solution containing a polymer represented by formula (I) or (II) and crosslinking the polymer:

$$(R^1)_x(OR^2)_{3-x}\text{Si-L}_1\text{-(A)-L}_2\text{-Si}(OR^3)_{3-y}(R^4)_y \quad \text{Formula (I)}$$

$$(R^5)_z(OR^6)_{3-z}\text{Si-L}_3\text{-(B)—R}^7 \quad \text{Formula (II)}$$

wherein $R^1$ to $R^6$ each independently represents a hydrogen atom or a hydrocarbon group having 8 or fewer carbon atoms; $R^7$ represents a hydrogen atom or a monovalent nonmetal atomic group; x, y, and z each independently represents an integer from 0 to 2; $L^1$ to $L^3$ each independently represents a divalent linking group having 3 or more types of atoms selected from the group consisting of a carbon atom, a hydrogen atom, an oxygen atom, a nitrogen atom, and a sulfur atom; and A and B each independently represents a polymer and an oligomer having structural unit repeats.

11. A method for producing the biochemical instrument according to claim 1 which comprises coating the surface of a water-insoluble material with a solution containing a polymer represented by formula (III) or (IV) and crosslinking the polymer:

$$(R^1)_x(OR^2)_{3-x}\text{Si-L}_1\text{-(CH}_2\text{CH}_2\text{O)}_n\text{-L}_2\text{-Si}(OR^3)_{3-y}(R^4)_y \quad \text{Formula (III)}$$

$$(R^5)_z(OR^6)_{3-z}\text{Si-L}_3\text{-(CH}_2\text{CH}_2\text{O)}_m\text{—R}^7 \quad \text{Formula (IV)}$$

n=3 to 25,000; m=3 to 25,000 wherein $R^1$ to $R^6$ each independently represents a hydrogen atom or a hydrocarbon group having 8 or fewer carbon atoms; $R^7$ represents a hydrogen atom or a monovalent nonmetal atomic group; x, y, and z each independently represents an integer from 0 to 2; and $L^1$ to $L^3$ each independently represents a divalent linking group having 3 or more types of atoms selected from a carbon atom, a hydrogen atom, an oxygen atom, a nitrogen atom, and a sulfur atom.

12. The method according to claim 10, wherein crosslinking is carried out by the sol-gel method.

13. The biochemical instrument according to claim 7, wherein crosslinking is carried out by the sol-gel method.

* * * * *